United States Patent
Schweitzer

(10) Patent No.: US 10,360,995 B2
(45) Date of Patent: Jul. 23, 2019

(54) SYSTEM AND METHOD FOR PARTITIONING CHEMOMETRIC ANALYSIS

(75) Inventor: Robert Schweitzer, Pittsburgh, PA (US)

(73) Assignee: ChemImage Technologies LLC, Pittsburgh, PA (US)

( * ) Notice: Subject to any disclaimer, the term of this patent is extended or adjusted under 35 U.S.C. 154(b) by 1555 days.

(21) Appl. No.: 11/918,486

(22) PCT Filed: Feb. 23, 2006

(86) PCT No.: PCT/US2006/006213
§ 371 (c)(1),
(2), (4) Date: Jan. 6, 2009

(87) PCT Pub. No.: WO2006/112944
PCT Pub. Date: Oct. 26, 2006

(65) Prior Publication Data
US 2009/0171593 A1 Jul. 2, 2009
US 2019/0026439 A9 Jan. 24, 2019

Related U.S. Application Data

(63) Continuation of application No. PCT/US2005/013036, filed as application No. PCT/US2006/006213 on Feb. 23, 2006.

(51) Int. Cl.
*G01N 33/48* (2006.01)
*G01N 33/50* (2006.01)
(Continued)

(52) U.S. Cl.
CPC ......... *G16C 20/20* (2019.02); *G01N 21/359* (2013.01); *G01N 21/3577* (2013.01);
(Continued)

(58) Field of Classification Search
None
See application file for complete search history.

(56) References Cited

U.S. PATENT DOCUMENTS 4,660,151 A 4/1987 Chipman et al.
4,701,838 A 10/1987 Swinkels et al.
(Continued)

FOREIGN PATENT DOCUMENTS

| EP | 0807809 | 11/1997 |
|----|---------|---------|
| WO | 8501348 | 3/1985 |
| WO | 2014074569 A1 | 5/2014 |

OTHER PUBLICATIONS

Windig et al. Combined use of conventional and second-derivative data is the SIMPLISMA self-modeling mixture analysis approach. Analytical Chemistry, 2002, vol. 74, pp. 1371-1379.*
(Continued)

*Primary Examiner* — Russell S Negin
(74) *Attorney, Agent, or Firm* — Pepper Hamilton LLP

(57) ABSTRACT

In one embodiment, the disclosure relates to a method for conducting a spectral library search to identify an unknown compound by acquiring one or more spectra of the compound; representing each spectrum as a target vector; providing an n-dimensional space having a plurality of partitioned spaces, at least one of the partitioned spaces containing at least one known vector representing a known material; mapping each target vector in one of the plurality of the partitioned spaces to form a mapped partitioned space; identifying one or more known vectors within the mapped partitioned space which approximate the target vector; and identifying the unknown compound by comparing the target vector to the known vectors within the mapped partitioned space which closely approximate the target vector.

42 Claims, 5 Drawing Sheets

(51) Int. Cl.
| | |
|---|---|
| *G16C 20/20* | (2019.01) |
| *G01N 21/359* | (2014.01) |
| *G01N 21/64* | (2006.01) |
| *G01N 21/65* | (2006.01) |
| *G01N 21/3577* | (2014.01) |
| *G01N 21/35* | (2014.01) |

(52) U.S. Cl.
CPC .............. *G01N 21/64* (2013.01); *G01N 21/65* (2013.01); *G01N 21/35* (2013.01)

(56) References Cited

U.S. PATENT DOCUMENTS

| | | |
|---|---|---|
| 4,766,551 A | 8/1988 | Begley |
| 4,885,697 A | 12/1989 | Hubner |
| 5,121,337 A | 6/1992 | Brown |
| 5,121,338 A | 6/1992 | Lodder |
| 5,124,932 A | 6/1992 | Lodder |
| 5,331,445 A | 7/1994 | Dickson et al. |
| 5,481,476 A | 1/1996 | Windig |
| 5,606,164 A | 2/1997 | Price et al. |
| 5,610,836 A | 3/1997 | Alsmeyer et al. |
| 5,684,580 A | 11/1997 | Cooper et al. |
| 5,710,713 A | 6/1998 | Wright et al. |
| 5,822,219 A | 10/1998 | Chen et al. |
| 6,341,257 B1 | 1/2002 | Haaland |
| 6,490,530 B1 | 12/2002 | Wyatt |
| 6,549,861 B1 | 4/2003 | Mark et al. |
| 6,584,413 B1 | 6/2003 | Keenan et al. |
| 6,675,106 B1 | 1/2004 | Keenan et al. |
| 6,959,248 B2 | 10/2005 | Gard et al. |
| 7,990,533 B2 | 8/2011 | Maier et al. |
| 8,167,794 B2 | 5/2012 | Matsumoto et al. |
| 2003/0229456 A1* | 12/2003 | Beger et al. .................... 702/27 |
| 2004/0220749 A1* | 11/2004 | Miller et al. .................... 702/19 |
| 2012/0083678 A1 | 4/2012 | Drauch et al. |
| 2013/0176568 A1 | 7/2013 | Priore et al. |
| 2016/0213252 A1 | 7/2016 | Hillman et al. |

OTHER PUBLICATIONS

Division, one page, 2008. The Columbia Encyclopedia, New York: Columbia University Press. Retrieved online on Nov. 14, 2011 from <<http://www.credoreference.com/entry/columency/division_in_mathematics>>.*

Extended European Search Report, Appiication No. 06735747.5, dated Nov. 28, 2008.

Caetano et al, Evaluation of the Importance of Non-Linear Spectral Mixing in Coniferous Forests, SPIE vol. 3499, pp. 257-269.

Rasmussen et al, Library Retrieval of Infrared Spectra Based on Detailed Intensity Information, Applied Spectroscopy, vol. 33, pp. 371-376.

Guilment et al. Infrared Chemical Micro-Imaging Assisted by Interactive Self Modeling Multivariate Analysis, Applied Spectroscopy, vol. 48. pp. 320-326.

Malinowski, Factor Analysis in Chemistry, 1991, 2nd edition.

Press et al, Numerical Recipes in C, the Art of Scientific Computing, 2nd edition.

Wang et al., Three-Dimensional Imaging of Ureter With Endoscopic Optical Coherence Tomography, Urology (May 2011), 77(5):1254-1258.

Caetano et al.; Evaluation of the Importance of Non-Linear Spectral Mixing in Coniferous Forests; Sep. 1998; SPIE vol. 3499; pp. 257-269.

Rasmussen et al.; Library Retrieval of Infrared Spectra Based on Detailed Intensity Information; Nov. 4, 1979; Applied Spectroscopy; vol. 33, pp. 371-376.

Guilment et al.; Infrared Chemical Micro-Imaging Assisted by Interactive Self-Modeling Multivariate Analysis; Nov. 3, 1994; Applied Spectroscopy; vol. 48, pp. 320-326.

Malinowski; Factor Analysis in Chemistry; Jan. 1991; second edition: published by John Wiley & Sons, Inc.

Press et al.; Numerical Recipes in C, The Art of Scientific Computing; Second Edition; originally published Jun. 1992-latest publication date 2002; published by Press Syndicate of the University of Cambridge.

* cited by examiner

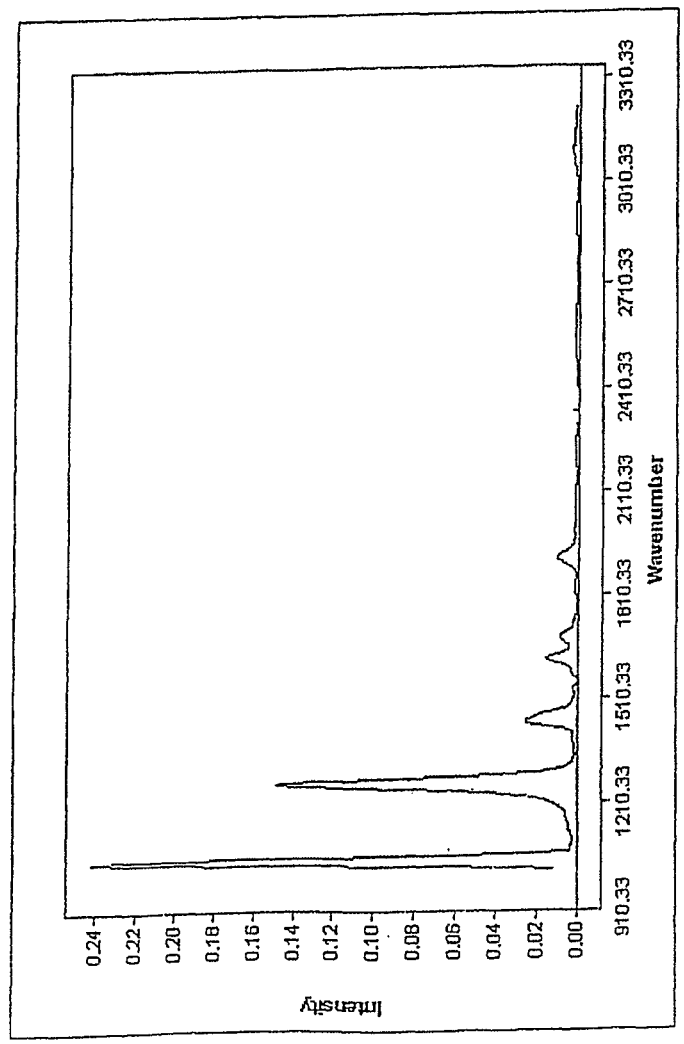
Fig. 2A Baking Soda

Corn Starch

Microcrystalline Cellulose

Cane Sugar

SYSTEM AND METHOD FOR PARTITIONING CHEMOMETRIC ANALYSIS

This application is a U.S. national stage filing under 35 U.S.C. § 371 of International Application No. PCT/US2006/006213, filed Feb. 23, 2006, which is a continuation application claiming the filing-date benefit of International Application No. PCT/US2005/013036 filed Apr. 15, 2005, the specification of each of these applications is incorporated herein in its entirety.

BACKGROUND

It is becoming increasingly important and urgent to rapidly and accurately identify toxic materials or pathogens with a high degree of reliability, particularly when the toxins/pathogens may be purposefully or inadvertently mixed with other materials. In uncontrolled environments, such as the atmosphere, a wide variety of airborne organic particles from humans, plants and animals occur naturally. Many of these naturally occurring organic particles appear similar to some toxins and pathogens even at a genetic level. It is important to be able to distinguish between these organic particles and the toxins/pathogens.

In cases where toxins and/or pathogens are purposely used to inflict harm or damage, they are typically mixed with so-called "masking agents" to conceal their identity. These masking agents are used to trick various detection methods and apparatus to overlook or be unable to distinguish the toxins/pathogens mixed therewith. This is a recurring concern for homeland security where the malicious use of toxins and/or infectious pathogens may disrupt the nation's air, water and/or food supplies. Additionally, certain businesses and industries could also benefit from the rapid and accurate identification of the components of mixtures and materials. One such industry that comes to mind is the drug manufacturing industry, where the identification of mixture composition could aid in preventing the alteration of prescription and non-prescription drugs.

One known method for identifying materials and organic substances contained within a mixture, or in elemental form, is to measure the absorbance, transmission, reflectance or emission of each material as a function of the wavelength or frequency of the illuminating or scattered light transmitted through the material. In the case of a mixture this requires that the mixture be separable into its component parts. Such measurements as a function of wavelength or frequency produce a plot that is generally referred to as a spectrum. The spectra of the material or object, i.e., sample spectra, can be identified by comparing the sample spectra to a set of reference spectra that have been individually collected for a set of known elements or materials. The set of reference spectra are typically referred to as a spectral library, and the process of comparing the sample spectra to the spectral library is generally termed a spectral library search.

Spectral library searches have been described in the literature for many years, and are widely used today. Spectral library searches using infrared (approximately 750 nm to 100 µm wavelength), Raman, fluorescence or near infrared (approximately 750 nm to 2500 nm wavelength) transmissions are well suited to identify many materials due to the rich set of detailed features these spectroscopy techniques generally produce. The above-identified spectroscopy techniques produce a rich fingerprint of the various pure entities and can be used to identify the component whether alone or in a mixture.

Conventional library searches generally and other such applications are time consuming and memory intensive. The process is also memory intensive because spectral libraries can be substantial in size. The instant application overcomes this and other problems by searching a sub-set of the library.

SUMMARY

In one embodiment, the disclosure relates to a method for determining an identity of an unknown material by (a) obtaining a spectrum of the material wherein the spectrum represents the unknown material; (b) representing the spectrum as a target vector; (c) providing a vector space containing a plurality of known vectors representing the spectra of known materials; (d) mapping the target vector into the vector space; (e) determining a correlation between the target and the known vectors; (f) identifying the unknown material as the known material based upon the determined correlation.

In another embodiment, the disclosure relates to a method for conducting a spectral library search to identify an unknown compound comprising acquiring one or more spectra of the compound; representing each spectrum as a target vector; providing an n-dimensional space having a plurality of partitioned spaces, at least one of the partitioned spaces containing at least one known vector representing a known material; mapping each target vector in one of the plurality of the partitioned spaces to form a mapped partitioned space; identifying one or more known vectors within the mapped partitioned space which approximate the target vector; and identifying the unknown compound by comparing the target vector to the known vectors within the mapped partitioned space which closely approximate the target vector.

In still another embodiment, the disclosure relates to a system for identifying the composition of an unknown material comprising: acquiring one or more spectra of the unknown material; a processor programmed with a first instruction for representing each spectrum as a target vector; a database for providing a plurality of partitioned spaces, at least one of the partitioned spaces containing at least one known vector representing a known material; the processor programmed with second instruction for: (i) mapping one of the target vectors in one of the partitioned spaces to form a mapped partitioned space; (ii) identifying one or more known vectors within the mapped partitioned space which approximate the target vector; and (iii) determining the identification of the unknown material by selecting a candidate which provides the closes approximation to the target vector of the unknown material.

In still another embodiment, the disclosure relates to a method for identifying of an unknown material comprising acquiring one or more spectrum of the unknown material; representing each spectrum as a target vector; providing a plurality of partitioned spaces, wherein at least one of said partitioned spaces contains at least one known vector representing a known material; mapping one of the target vectors into one of the partitioned spaces to form a mapped partitioned space; identifying at least one known vector within the mapped partitioned space which approximates the target vector; identifying adjacent mapped partitioned spaces having at least one vector approximating the target vector; and calculating a correlation between the target spectrum and the known vectors in the partitioned space and the adjacent known partitioned spaces to identify the best candidate.

In yet another embodiment, the disclosure relates to a system for identifying of an unknown material comprising acquiring one or more spectra of the unknown material; a processor programmed with a first set of instructions for representing each spectrum as a target vector; a database for providing a plurality of partitioned spaces, wherein at least one of said partitioned spaces contains at least one known vector representing a known material; the processor programmed with a second set of instructions for: (i) mapping one of the target vectors into one of the partitioned spaces to form a mapped partitioned space; (ii) identifying at least one known vector within the mapped partitioned space which approximates the target vector; (iii) identifying adjacent mapped partitioned spaces having at least one vector approximating the target vector; and (iv) calculating a correlation between the target spectrum and the known vectors in the partitioned space and the adjacent known partitioned spaces to identify the best candidate.

BRIEF DESCRIPTION OF THE DRAWINGS

FIG. 2A is a spectral representation of baking soda.

DETAILED DESCRIPTION

Figure 1:
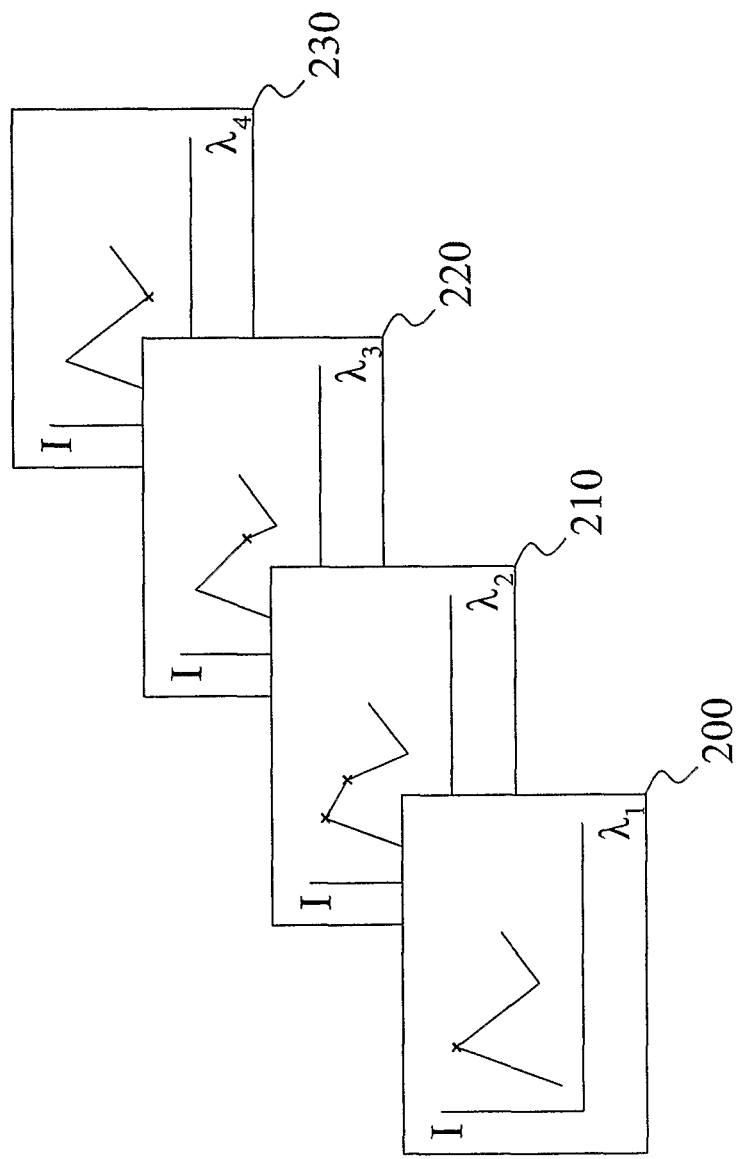
FIG. 1 schematically shows an exemplary spectrum for a pixel.

A chemical image is compiled from several frames having a plurality of spectra. A pixel of the image can be deconstructed into a plurality of frames where each frame of the pixel denotes a relationship between intensity and wavelength (or wave-number). FIG. 1 schematically shows an exemplary spectrum for a pixel. As can be seen from FIG. 1, the spectral representation of a pixel shows the intensity and wave-number relationship for the pixel at wave-numbers common to all spectra of the sample.

Figure 2B:
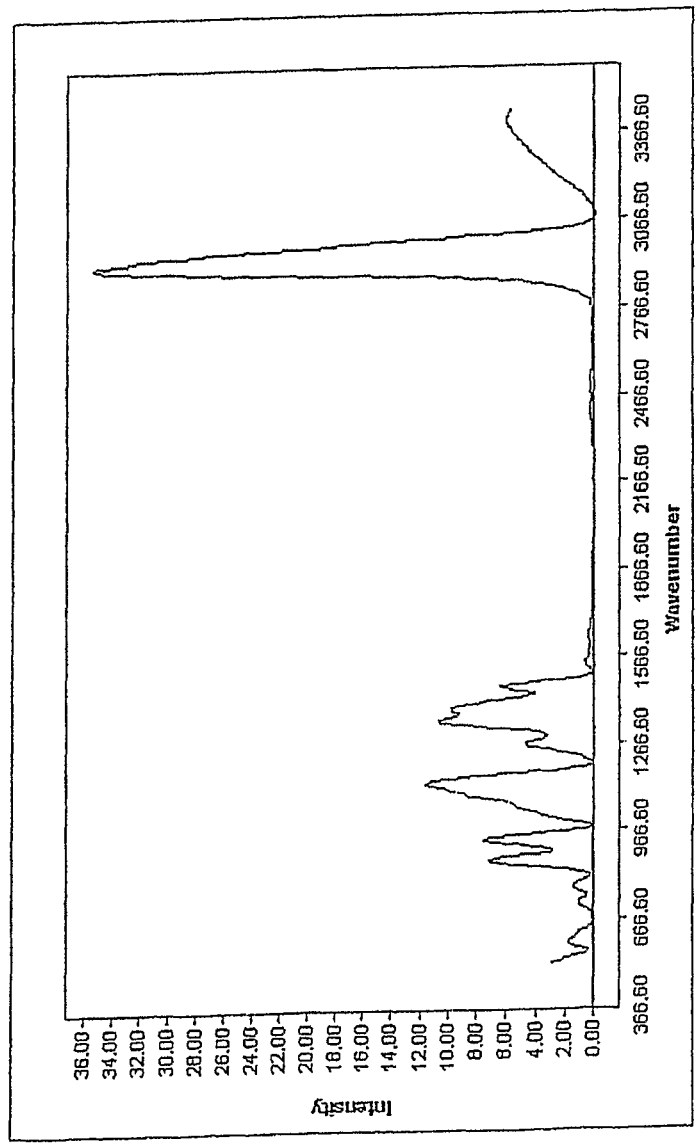
FIG. 2B is a spectral representation of corn starch.
Figure 2C:
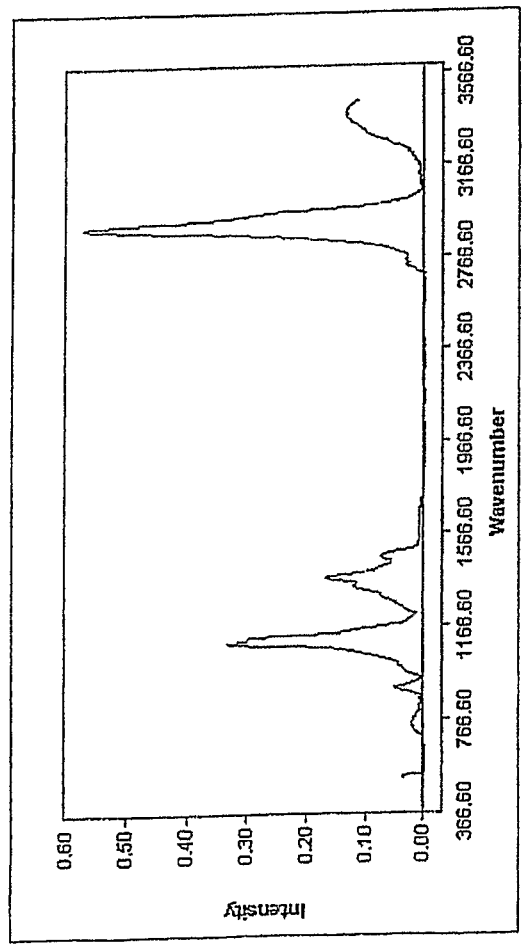
FIG. 2C is a spectral representation of microcrystalline cellulose.
Figure 2D:
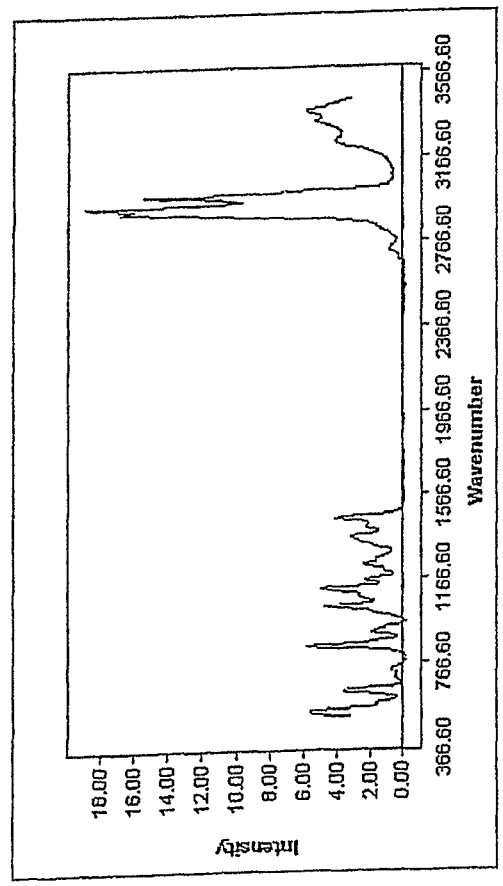
FIG. 2D is a spectral representation of cane sugar.

FIGS. 2A-2D are spectral representations of common substances which exist as white powders. Specifically, FIG. 2A is the spectral representation of baking soda; FIG. 2B is the spectral representation of corn starch; FIG. 2C is the spectral representation of microcrystalline cellulose and FIG. 2D is the spectral representation of cane sugar. The spectra of other substances are readily available and can be compiled in a library of spectra.

The spectrum can be collected using various spectroscopical techniques, including infrared, Raman, Fluorescence and near infrared techniques. The spectra of many materials are often collected in a library of known materials. The library spectra should be corrected to remove all signals and information that are not due to the chemical compositions of the samples and known elements/material. Such anomalies include various instrumental effects, such as the transmission of optical elements, the detector's responsiveness, and any other non-desired sample effect due to the instrument utilized for collecting the spectra. It is noted that the uncorrected spectra may also be used without departing from the principles disclosed herein. Thus, an optional step according to an embodiment of the disclosure may include removing instrument-dependent error from the spectra and/or the library. This step can be implemented by using the transfer function of the instrument.

PCA is a data dimensionality reduction technique based on a multivariate least-squares calculation. It is similar to an Eigenvector analysis calculation (typically associated with the mathematical field of linear algebra). PCA results in the representation of a set of data by a reduced set of factors where some percentage of the variance of the data set is explained (typically 95, 99, or 99.5%). Thus, the relative position of the points in the reduced n-dimensional space with respect to each other is unchanged relative to the position of the points in the original-dimensional space to the extent that the variance of the data set is explained. In practical terms, this means that a set of spectra can be represented by a greatly reduced set of abstract factors (alternatively termed principal components or eigenvectors). Typically a set of 1024 spectral point spectra can be represented as a set of 10-15 point abstract factors with virtually no loss in accuracy. This reduction allows the partitioning of a dataspace with much smaller numbers of dimensions than the original dataspace. Without this reduction, the n-dimensional partitioning would not be practical for most spectral data sets.

In one embodiment of the disclosure an n-dimensional space (or a partitioned space) is used to relate the unknown composition with the known materials. In contrast with the conventional library searches, this method provides an expedited operation. An n-dimensional space can have any general form, for example, a sphere with multiple axial vectors intercepting at one point in space. For the sake of simplicity, the inventive concepts will be discussed in relation to a three-dimensional space; however, the disclosure is not limited thereto. Extending the inventive concepts from a three-dimensional space to an n-dimensional space is well within the skill of one of ordinary skill in the art.

According to one embodiment of the disclosure, the identity of an unknown material can be detected by obtaining a spectrum of the material. This step can be implemented using any conventional spectroscopic device. Next, the spectrum can be reduced to one or more target vectors. Conventional algorithms, such as those identified above including PCA, can be used for reducing the spectrum to a target vector. To determine the identity of the unknown material a vector space containing a plurality of known vectors can be then provided. The vector space can be an n-dimensional space containing the spectra of known components in the vector form. In other words, the n-dimensional space can be constructed around one or more vectors representing spectra of known material. Such vectors can be defined based on the spectra of known material. For example, an n-dimensional space can be constructed based on vectors representing such known material as sugar, flour, salt, anthrax, etc. Each known vector defines a point of origin and an end point, which in turn define direction and magnitude of the vector. A plurality of such vectors then form an n-dimensional space within which the spectrum of the known material (i.e., the unknown spectrum) can be identified.

Once the n-dimensional space is constructed, the unknown spectrum (interchangeably, the target vector) can be mapped into the vector space. Typically, the target vector is mapped such that the vector's origin is consistent with the origin of the other known vectors. The target vector then extends in a particular direction to its end point in the vector space. Once mapped into the vector space, a correlation between the target vector and one or more the known vectors can be determined. Such correlation may be, for example, mathematical or geometrical. Once a correlation between the target vector and at least one known vector is determined, the identity of the unknown material can be readily ascertained.

Accordingly to one embodiment of the disclosure, the process of correlating the target and the known vector can be implemented by partitioning the vector space into sub-spaces (interchangeably, partitioned spaces) containing one or more of the known vectors. The sub-spaces can have any form. In one embodiment, the sub-spaces define cubes of consistent size. Moreover, each sub-space can have one or more known vectors thereon. The partitioning of the n-dimensional space into a set of subspaces is performed by the following steps. 1) A minimum and maximum value is determined for each coordinate axis in the n-dimensional space (based on the projection of the known vectors onto that axis). 2) Each coordinate axis that has a length greater than some minimum length (based on the range of the coordinate axis with the largest range) is then divided by an integer M. 3) The resultant divided coordinate axes form a set of subspaces in the n-dimensional space. 4) M is generally set to 2 initially and is incremented by increments of 1 until the desired degree of partitioning is reached. 5) The degree of partitioning is determined by the density of the number of known vectors that map into any given subspace.

After the sub-spaces are defined, the identity of the target vector can be determined by correlating the target vector to an appropriate sub-space. For example, for one of the sub-spaces into which the target vector is mapped, a correlation between the target vector and each of the known vectors in said sub-space can be determined. The identity of the unknown vector can be then determined based on such a correlation.

In one exemplary embodiment, the step of providing a plurality of partitioned spaces includes providing an n-dimensional space with a plurality of known vectors in n-dimensions. Each of the coordinate axes of the n-dimensional space can then be divided by an integer M to get a set of n-dimensional subspaces where each n-dimensional subspace is populated by a plurality of the known vectors. Next, a ratio of known vectors occupying each n-dimensional subspace as a percentage of a total number of known vectors can be determined. Once such ratio is defined, the n-dimensional space can be divided into further sub-spaces if the ratio of the known vectors in any of the n-dimensional subspace exceeds a threshold. This process is aided by finding a minimum point and a maximum point for each of the coordinate axes. In an alternative embodiment, the threshold can be selected algorithmically. The threshold can have any range. For example, the threshold can be in the range of 20-80&, 5-90% or 1-99%.

The embodiments described above can be implemented with a processor in communication with a database and other electronic peripherals. For example, an image forming spectra of an unknown material can be first obtained. Each spectra is a function of at least one of intensity, wavelength, wave number or frequency. Next, a processor can be programmed with a set of instructions to represent each spectrum as a target vector. The processor can communicate with a database for providing a plurality of partitioned spaces, each partitioned space containing at least one known vector representing a known component. The same or a different processor can also be programmed with a second set of instructions for, among others, (1) mapping one of the target vectors in one of the partitioned spaces to form a mapped partitioned space; (2) identifying one or more known vectors within the mapped partitioned space which approximate the target vector; and (3) determining the identity of the unknown material by selecting a candidate which provides the closest approximation to the target vector of the unknown material. According to this embodiment, the step of mapping each target vector to one of the plurality of partitioned spaces may further include representing each target data point as a vector; and identifying each n-dimensional space where the target vector resides.

The embodiments disclosed herein are exemplary in nature and are intended to illustrate, not limit, applicant's inventive principles.

What is claimed is:

1. A computer-implemented method for identifying an unknown material, the method comprising, by a processor:
   providing a vector space comprising a plurality of known vectors representing a plurality of spectra of known materials;
   partitioning the vector space into a plurality of subspaces according to a degree of partitioning determined based on a density of the plurality of known vectors, the plurality of subspaces comprising at least one of the plurality of known vectors, wherein partitioning the vector space comprises:
      determining a ratio of known vectors occupying each of a first plurality of partitioned subspaces as a percentage of a total number of known vectors, and
      further subdividing the vector space into a second plurality of partitioned subspaces if the ratio exceeds a threshold;
   accessing a spectrum of the unknown material;
   reducing the spectrum to generate a target vector;
   mapping the target vector into one of the first or second plurality of subspaces;
   searching the subspace into which the target vector is mapped to determine a correlation between the target vector and each of the plurality of known vectors in the subspace; and
   identifying the unknown material based on the correlation.

2. The method of claim 1, further comprising: repeating the searching and the identifying at least once.

3. A computer-implemented method for conducting a spectral library search to identify an unknown compound comprising, by a processor:
   accessing at least one spectrum of the unknown compound;
   representing the at least one spectrum as a target vector;
   providing an n-dimensional space having a plurality of partitioned subspaces representing a plurality of known vectors of known materials, each of the plurality of partitioned subspaces comprising at least one of the plurality of known vectors, the n-dimensional space being partitioned according to a degree of partitioning determined based on a density of the plurality of known vectors, wherein providing the n-dimensional space comprises:
      determining a ratio of known vectors occupying each of the first plurality of partitioned subspaces as a percentage of a total number of known vectors, and
      further subdividing the n-dimensional space into a second plurality of partitioned subspaces if the ratio exceeds a threshold;
   mapping each target vector to one of the first or second plurality of the partitioned subspaces to form a mapped partitioned subspace;
   identifying one or more known vectors which approximate the target vector; and
   identifying the unknown compound by searching within the mapped partitioned subspace to identify a known vector which is a closest approximation to the target vector.

4. The method of claim 3, wherein the target vector is generated through principal component analysis.

5. The method of claim 3, wherein providing the n-dimensional space further comprises:
configuring the n-dimensional space to have the plurality of known vectors in n-dimensions;
finding a minimum point and a maximum point for each coordinate axes of the n-dimensional space; and
dividing each of the coordinate axes of the n-dimensional space by a positive integer M to provide the first plurality of partitioned subspaces, wherein at least one of the first plurality of partitioned subspaces comprises a known vector.

6. The method of claim 5, further comprising finding a minimum point and a maximum point for each of the plurality of known vectors.

7. The method of claim 3, wherein the threshold is selected algorithmically.

8. The method of claim 3, wherein the threshold is in the range of 5-90%.

9. The method of claim 3, wherein mapping the target vector further comprises:
representing each target data point as a data point target vector; and
identifying each of the plurality of partitioned subspaces where the data point target vector resides.

10. The method of claim 3, wherein the at least one spectrum is a function of at least one of intensity, wavelength, wave number, frequency, and combinations thereof.

11. A system for identifying the composition of an unknown material comprising:
a processor in operable communication with a spectroscopic device configured to acquire at least one spectrum of the unknown material; and
a non-transitory, computer-readable storage medium in operable communication with the processor, wherein the computer-readable storage medium contains one or more programming instructions that, when executed, cause the processor to:
receive the at least one spectrum,
represent the at least one spectrum as a target vector,
provide a plurality of partitioned subspaces representing a plurality of known vectors of known materials, each of the plurality of partitioned subspaces comprising at least one of the plurality of known vectors, the plurality of partitioned subspaces being partitioned according to a degree of partitioning determined based on a density of the plurality of known vectors, wherein providing the plurality of partitioned subspaces comprises:
determining a ratio of known vectors occupying each of a first plurality of partitioned subspaces as a percentage of a total number of known vectors, and
further subdividing the n-dimensional space into a second plurality of partitioned subspaces if the ratio exceeds a threshold,
map the target vector to one of the first or second plurality of partitioned subspaces to form a mapped partitioned subspace, search within the mapped partitioned subspace to identify one or more known vectors which approximate the target vector, and
identify the unknown material by selecting a known vector which provides a closest approximation to the target vector.

12. The system of claim 11, wherein the target vector defines a set of points in the at least one spectrum.

13. The system of claim 11, wherein the target vector is generated through principal component analysis.

14. The system of claim 11, wherein providing a plurality of partitioned subspaces further comprises:
providing an n-dimensional space having the plurality of known vectors in n-dimensions;
finding a minimum point and a maximum point for each coordinate axes of the n-dimensions; and
dividing each of the coordinate axes by a positive integer M to provide the first plurality of partitioned subspaces, wherein at least one of the first plurality of partitioned subspaces comprises at least one of the plurality of known vectors.

15. The system of claim 11, wherein the threshold is selected algorithmically.

16. The system of claim 11, wherein the threshold is in the range of 5-90%.

17. The system of claim 11, wherein mapping the target vector further comprises representing each target data point as a data point target vector and identifying each of the plurality of partitioned subspaces where the data point target vector resides.

18. The system of claim 11, wherein the at least one spectrum is a function of at least one of intensity, wavelength, wave number, frequency, and combinations thereof.

19. An apparatus for conducting a spectral library search to identify an unknown material comprising:
a spectroscopic device configured to acquire at least one spectrum of the unknown material;
a processor in operable communication with the spectroscopic device; and
a non-transitory, computer-readable storage medium in operable communication with the processor, wherein the computer-readable storage medium contains one or more programming instructions that, when executed, cause the processor to:
receive the at least one spectrum,
represent the at least one spectrum as at least one target vector,
provide an n-dimensional space with a plurality of partitioned subspaces representing a plurality of known vectors of known materials, each of the plurality of partitioned subspaces comprising at least one of the plurality of known vectors, the n-dimensional space being partitioned according to a degree of partitioning determined based on a density of the plurality of known vectors, wherein providing an n-dimensional space comprises:
determining a ratio of known vectors occupying each of a first plurality of partitioned subspaces as a percentage of a total number of known vectors, and
further subdividing the n-dimensional space into a second plurality of partitioned subspaces if the ratio exceeds a threshold,
mapping the at least one target vector to one of the first or second plurality of the partitioned subspaces to form a mapped partitioned subspace,
identify one or more known vectors within the mapped partitioned subspace which approximate the target vector, and
identify the unknown material by searching the mapped partitioned subspace to identify a known vector that provides a closest approximation to the target vector.

20. The apparatus of claim 19, wherein the target vector is generated through principal component analysis.

21. The apparatus of claim 19, wherein providing the n-dimensional space comprises:
    configuring the n-dimensional space to have the plurality of known vectors in n-dimensions;
    finding a minimum point and a maximum point for each coordinate axes of the n-dimensional space; and
    dividing each of the coordinate axes of the n-dimensional space by a positive integer M to provide the first plurality of partitioned subspaces, wherein at least one of the first plurality of partitioned subspaces comprises at least one of the known vectors.

22. The apparatus of claim 21, further comprising finding the minimum point and the maximum point for each of the plurality of known vectors.

23. The apparatus of claim 19, wherein the threshold is selected algorithmically.

24. The apparatus of claim 19, wherein the threshold is in the range of 5-90%.

25. The apparatus of claim 19, wherein mapping the at least one target vector to one of the plurality of partitioned subspaces further comprises representing each target data point as a data point target vector and identifying a partitioned subspace where the data point target vector resides.

26. The apparatus of claim 19, wherein the at least one spectrum is a function of at least one of intensity, wavelength, wave number, frequency, and combinations thereof.

27. A computer-implemented method for identifying an unknown material, the method comprising, by a processor:
    accessing at least one spectrum of the unknown material;
    representing the at least one spectrum as a target vector;
    providing a plurality of partitioned subspaces representing a plurality of known vectors of known materials, wherein at least one of said plurality of partitioned subspaces comprises at least one known vector representing a known material, wherein providing the plurality of partitioned subspaces comprises:
        determining a ratio of known vectors occupying each of a first plurality of partitioned subspaces as a percentage of a total number of known vectors, and
        further subdividing the n-dimensional space into a second plurality of partitioned subspaces if the ratio exceeds a threshold;
    map the target vector to one of the first or second plurality of partitioned subspaces to form a mapped partitioned subspace;
    identify at least one of the plurality of known vectors within the mapped partitioned subspace which approximates the target vector;
    identify adjacent mapped partitioned subspaces having at least one vector approximating the target vector; and
    calculate a correlation between the target vector and each of the plurality of known vectors in the plurality of partitioned subspaces and the adjacent mapped partitioned subspaces;
    identify the unknown material based on the correlation.

28. The method of claim 27, wherein the target vector defines a set of points in the at least one spectrum.

29. The method of claim 27, wherein the target vector is generated through principal component analysis.

30. The method of claim 27, wherein providing a plurality of partitioned subspaces further comprises:
    providing an n-dimensional space having a plurality of known vectors in n-dimensions;
    finding a minimum point and a maximum point of each coordinate axes of the n-dimensional space; and
    dividing each of the coordinate axes of the n-dimensional data space by a positive integer M to provide the first plurality of partitioned subspaces, wherein at least one of the subspaces comprises at least one of the plurality of known vectors.

31. The method of claim 27, wherein the threshold is selected algorithmically.

32. The method of claim 27, wherein the threshold is in the range of 5-90%.

33. The method of claim 27, wherein mapping the target vector further comprises representing each target data point as a data point target vector and identifying each of the plurality of partitioned subspaces where the data point target vector resides.

34. The method of claim 27, wherein the at least one spectrum is a function of at least one of intensity, wavelength, wave number, frequency, and combinations thereof.

35. A system for identifying of an unknown material comprising;
    a processor in operable communication with a spectroscopic device configured to acquire at least one spectrum of the unknown material;
    a non-transitory, computer-readable storage medium in operable communication with the processor, wherein the computer-readable storage medium contains one or more programming instructions that, when executed, cause the processor to:
    receive the at least one spectrum,
    represent the at least one spectrum as a target vector,
    provide a plurality of partitioned subspaces representing a plurality of known vectors of known materials, each of the plurality of partitioned subspaces comprising at least one of the plurality of known vectors, the plurality of partitioned subspaces being partitioned according to a degree of partitioning determined based on a density of the plurality of known vectors, wherein providing the plurality of partitioned subspaces comprises:
        determining a ratio of known vectors occupying each of the first plurality of partitioned subspaces as a percentage of a total number of known vectors, and
        further subdividing the n-dimensional space into a second plurality of subspaces if the ratio exceeds a threshold,
    map the target vector to one of the first or second plurality of partitioned subspaces to form a mapped partitioned subspace,
    search within the mapped partitioned subspace to identify one or more known vectors which approximate the target vector,
    identify adjacent mapped partitioned subspaces having at least one vector approximating the target vector,
    calculate a correlation between the target vector and each of the plurality of known vectors in the plurality of partitioned subspaces and the adjacent mapped partitioned subspaces, and
    identifying the unknown material based on the correlation.

36. The system of claim 35, wherein the target vector defines a set of points in the at least one spectrum.

37. The system of claim 35, wherein the target vector is generated through principal components analysis.

38. The system of claim 35, wherein providing a plurality of partitioned spaces further comprises:
    providing an n-dimensional space having the plurality of known vectors in n-dimensions
    finding a minimum point and a maximum point of each coordinate axes of the n-dimensional space; and dividing each of the coordinate axes of the n-dimensional data space by a positive integer M to provide the first plurality of partitioned subspaces, wherein at least one of the subspaces comprises at least one of the plurality of known vectors.

39. The system of claim 35, wherein the threshold is selected algorithmically.

40. The system of claim 35, wherein the threshold is in the range of 5-90%.

41. The system of claim 35, wherein mapping the target vector further comprises representing each target data point as a data pint target vector and identifying each of the plurality of partitioned subspaces where the data point target vector resides.

42. The system of claim 35, wherein the at least one spectrum is a function of at least one of intensity, wavelength, wave number, frequency, and combinations thereof.

* * * * *